US012702366B2

(12) United States Patent
Wicklein et al.

(10) Patent No.: US 12,702,366 B2
(45) Date of Patent: Aug. 11, 2026

(54) BREAST FIXATION ELEMENT

(71) Applicant: Siemens Healthineers AG, Forchheim (DE)

(72) Inventors: Julia Wicklein, Erlangen (DE); Madeleine Hertel, Forchheim (DE); Magdalena Herbst, Erlangen (DE); Zhenzhen Jiang, Erlangen (DE); Steffen Kappler, Effeltrich (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 235 days.

(21) Appl. No.: 18/360,917

(22) Filed: Jul. 28, 2023

(65) Prior Publication Data

US 2024/0032878 A1 Feb. 1, 2024

(30) Foreign Application Priority Data

Jul. 29, 2022 (DE) ..................... 10 2022 207 880.2

(51) Int. Cl.
*A61B 6/04* (2006.01)

(52) U.S. Cl.
CPC ................................. *A61B 6/0435* (2013.01)

(58) Field of Classification Search
CPC ...... A61B 6/0435; A61B 6/0414; A61B 6/502
See application file for complete search history.

(56) References Cited

U.S. PATENT DOCUMENTS

| | | | | |
|---|---|---|---|---|
| 4,691,333 A * | 9/1987 | Gabriele | ................ | A61B 6/502 5/601 |
| 6,577,702 B1 * | 6/2003 | Lebovic | ................. | A61B 6/502 378/68 |
| 11,944,458 B2 * | 4/2024 | Mullally | ................ | A61B 5/708 |
| 2003/0007597 A1 * | 1/2003 | Higgins | ............... | A61B 6/0414 378/37 |
| 2005/0113683 A1 * | 5/2005 | Lokhandwalla | ....... | A61B 6/502 128/915 |
| 2006/0165215 A1 * | 7/2006 | Galkin | ................... | A61B 6/502 378/37 |
| 2007/0223652 A1 * | 9/2007 | Galkin | ................... | A61B 7/045 378/37 |
| 2007/0280412 A1 * | 12/2007 | Defreitas | ............. | A61B 6/0414 378/37 |
| 2008/0043904 A1 * | 2/2008 | Hoernig | ................. | A61B 6/502 378/208 |
| 2008/0103387 A1 * | 5/2008 | Gross | ................... | A61B 6/4417 600/564 |
| 2008/0230074 A1 * | 9/2008 | Zheng | .................... | A61B 5/055 128/869 |

(Continued)

FOREIGN PATENT DOCUMENTS

| | | |
|---|---|---|
| DE | 102009056176 A1 | 6/2011 |
| JP | 2005348971 A | 12/2005 |

*Primary Examiner* — David J Makiya
*Assistant Examiner* — Soorena Kefayati
(74) *Attorney, Agent, or Firm* — Harness, Dickey & Pierce, P.L.C.

(57) ABSTRACT

One or more example embodiments of the present invention relates to a breast fixation element for a mammography system having a flat elastic surface element including a fastening element for fixing the breast to a support surface of the mammography system, wherein a shape of the breast fixation element is adapted to a shape of the breast.

15 Claims, 2 Drawing Sheets

(56) References Cited

U.S. PATENT DOCUMENTS

| | | | | |
|---|---|---|---|---|
| 2009/0135997 | A1* | 5/2009 | Defreitas | A61B 6/0414 378/37 |
| 2009/0213986 | A1* | 8/2009 | Thaler | A61B 6/0414 378/208 |
| 2009/0264709 | A1* | 10/2009 | Blurton | A61B 17/085 600/206 |
| 2010/0049093 | A1* | 2/2010 | Galkin | A61B 6/0485 600/586 |
| 2010/0128843 | A1* | 5/2010 | Tita | A61B 6/0414 378/208 |
| 2011/0129062 | A1* | 6/2011 | Hoernig | A61B 90/17 378/37 |

* cited by examiner 6
7
2
5
1
4
8
5
5

11
10
12
1
4
2
3

1
14
15

BREAST FIXATION ELEMENT

CROSS-REFERENCE TO RELATED APPLICATION(S)

The present application claims priority under 35 U.S.C. § 119 to German Patent Application No. 10 2022 207 880.2, filed Jul. 29, 2022, the entire contents of which are incorporated herein by reference.

FIELD

One or more example embodiments relates to a breast fixation element and a mammography system therefor, wherein the breast is fixed for radiography.

RELATED ART

In current mammography systems, the patient's breast or the breast of the examination object is compressed by special compression paddles before 2D imaging or tomosynthesis imaging is performed. These compression procedures are painful for the patient since they exert some pressure on the breast. The aim is to avoid as much overlap of the breast structures as possible. This is crucial for 2D imaging, but can be reduced for tomosynthesis imaging, in particular with a wide-angle system.

A mammography system comprises an X-ray source and an X-ray detector, wherein the breast is arranged between the X-ray source and the X-ray detector. The breast can usually be arranged on a surface of the housing of the X-ray detector.

SUMMARY

At present, compression paddles are the gold standard for mammography systems. Lower compression is possible, for example, with various optimized procedures. Reduction in pain during compression can, for example, be achieved by compression using inflatable cushions.

One or more example embodiments provides a breast fixation element and a mammography system which enable simplified and pain-free fixation of the breast.

This is provided by a breast fixation element as claimed in claim 1 and a mammography system as claimed in claim 14.

BRIEF DESCRIPTION OF THE DRAWINGS

The following explains exemplary embodiments of the invention in more detail with reference to drawings. The drawings show.

DETAILED DESCRIPTION

Figures 1, 2:
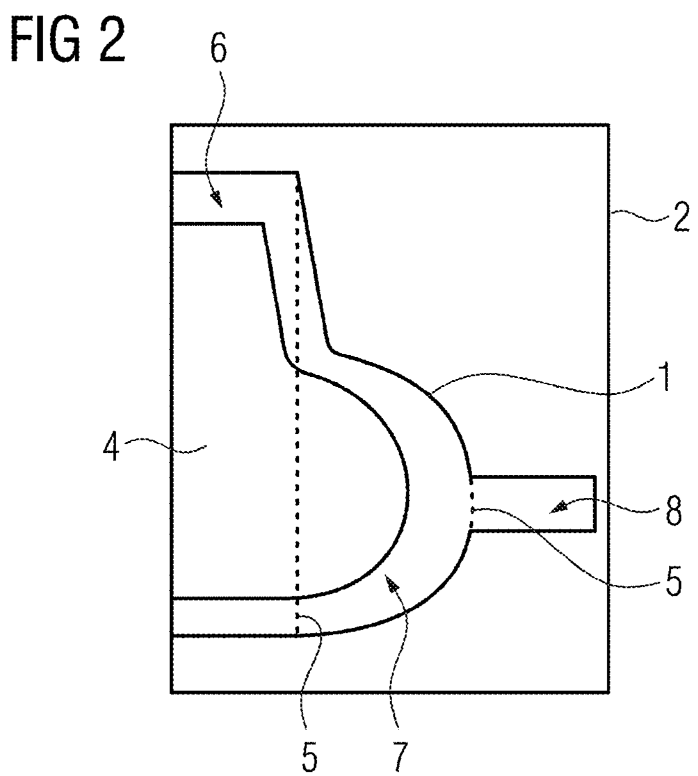
FIG. 1 a schematic representation of the breast fixation element according to the invention in a first embodiment.
FIG. 2 a schematic representation of the breast fixation element according to the invention in a second embodiment.

The invention relates to a breast fixation element for a mammography system having:

a flat elastic surface element with a fastening element for fixing the breast to a support surface of the mammography system, wherein the flat shape of the breast fixation element is adapted to the shape of a breast.

The breast fixation element can in particular be embodied as detachable. The breast can be arranged on the support surface, in particular a surface of the housing of the X-ray detector. The breast fixation element can first be applied to the breast. Herein, the breast fixation element, in particular the surface element, can nestle along the shape of the breast, preferably without substantially constricting the breast. The upper side of the breast and at least partially the side surfaces of the breast can be enclosed by the breast fixation element. A fastening element or a plurality of fastening elements can be provided. The surface element can be fastened to the support surface or connected to the support surface via the at least one fastening element. The breast fixation element can in particular be embodied for single use. This can advantageously enable cleaning of the breast fixation element to be avoided.

In one preferred embodiment, the breast fixation element can include the material of a kinesiology tape. Herein, the flat elastic surface element can be embodied as a fabric together with the fastening element as an adhesive surface.

Instead of breast compression, fixation can take place via kinesiology tape, which is usually used in the field of physiotherapy to stabilize the musculoskeletal system, for example in the case of athletes. These bands or tapes are available in various colors or uncolored. Preference should be given to a semi-transparent version of the kinesiology tape so that the fixed breast can be checked for skin folds. These tapes are already approved as a medical device and are latex-free and particularly kind to the skin. The adhesive tape or kinesiology tape can be removed from the breast painlessly and without leaving any residue; no traces of adhesive remain on the skin or on the detector cover.

To achieve the best fixation results, it can be particularly advantageous to manufacture or provide the surface element in the shape of a breast or adapted to the shape of the breast. The carrier material or the surface element can be perforated parallel to the chest wall in order to ensure successive fastening from the side of the chest wall in the direction of the nipple and beyond. Herein, the perforation can be embodied in a line parallel to the edge of the breast fixation element, which in use extends parallel to the chest wall. The perforation can in particular be embodied at a distance from the edge of the breast fixation element, wherein the distance can be selected such that at least more than half the breast volume can be arranged between the edge and the distance. Thus, in the sloping region of the breast toward the nipple, the shape of the breast fixation element can be adapted to the individual shape of the breast in a simplified manner via the perforation. Furthermore, different sizes and shapes of the breast fixation elements can be provided to enable a breast fixation element according to one or more example embodiments of the present invention to be used in a particularly advantageous manner for different breast sizes and different positions, such as craniocaudal and mediolateral (oblique) positions. A further perforation can be embodied in the region of the nipple parallel to the edge.

Viewed from the edge, the shape of the breast fixation element can comprise an initially rectangular region, the longer edge of which extends along the edge. The rectangular region can be adjoined by a rounded region, which, for example, can be embodied as approximately semicircular in shape. Herein, the edge of the semicircle can adjoin the rectangular region. This can be adjoined by a narrower second rectangular region in extension to the center of the semicircle, wherein the short edge of the second rectangular region adjoins the semicircle, wherein a perforation can be embodied at the transition between the semicircular region and the second rectangular region. Viewed from the first rectangular region, the semicircular region can be embodied as centered, in particular for an embodiment for craniocaudal imaging. Viewed from the first rectangular region, the semicircular region can be embodied as non-centered, in particular for an embodiment for mediolateral (oblique) imaging. The two rectangular regions can be used at least partially for fastening to the support surface, in particular the regions that overlap the breast.

Advantageously, the breast fixation element can stabilize the like a paddle, but without any pain due to compression. Fastening to the housing of the X-ray detector achieves good and improved spatial resolution in contrast to solutions with air cushions or the like. This solution is particularly suitable for wide-angle imaging in breast tomosynthesis, since compression is not mandatory, fast breast tomosynthesis imaging, breast tomosynthesis imaging with distributed sources, or the like.

Advantageously, fewer mechanical elements are required, wherein reduced costs result due to the omission of the paddle holder and foot switch. Advantageously, no paddle disinfection is required and time can be saved in clinical routine. Advantageously, paddle-induced scattering of X-rays can be avoided. Advantageously, paddle-induced artifacts can be avoided. Advantageously, the risk of injury from paddle breakage or bruising can be avoided.

According to one or more example embodiments of the present invention, the fastening element is embodied in the form of an adhesive layer embodied as substantially flat on the underside of the surface element. The adhesive layer can in particular be brought into contact, and thus connection, with the breast and with the support surface. The breast fixation element can in particular be embodied as an adhesive tape or kinesiology tape.

According to one or more example embodiments of the present invention, the breast fixation element comprises kinesiology tape. Kinesiology tape (or physio tape) is an elastic textile, in particular colored, adhesive tape. The textile can be applied to the carrier sheet (paper backing) with a ten percent stretch; it can be cotton fabric with spandex threads, viscose, or synthetic. The elasticity for the tapes is generally described as "stretchable to 130 to 140%" of the original length. Stretchability can be up to 180%. Herein, the tapes are primarily longitudinally elastic, but also obliquely elastic. The elasticity properties can be similar to those of human skin. Acrylate adhesive is applied to the carrier material as an adhesive layer in a wavy pattern; this is activated by body heat and rubbing. The tape is permeable to air and moisture. The breast fixation element can be provided as a pre-cut piece (a "pre-cut").

According to one or more example embodiments of the present invention, the breast fixation element comprises nylon, Lycra, elastic tape or cotton, in particular as a surface element. The material of the surface element can in particular be elastic so that it can be adapted to the shape of the breast. The material of the surface element can in particular be kind to the skin.

According to one or more example embodiments of the present invention, the shape of the surface element is adapted to the breast. The surface element and in particular the breast fixation element can—as described above—be composed of a rectangular element and a semicircular element. Here, the composition can in particular be restricted to the composition of the shape so that the breast fixation element is still produced in one piece.

According to one or more example embodiments of the present invention, the shape of the surface element is square, rectangular, round or triangular. The surface element, or in particular the breast fixation element, can have a simple geometric shape, which still allows adaptation to the shape of the breast. In addition, perforations can be provided. A perforation can increase stretchability. The surface element or the breast fixation element can be torn along a perforation thus enabling improved adaptation to the shape of the breast.

According to one or more example embodiments of the present invention, the fastening element includes an adhesive layer. In particular in the embodiment as a kinesiology tape, the fastening element can be embodied as an adhesive layer. Herein, the adhesive layer can preferably be embodied over the (whole) surface.

In an alternative embodiment, the adhesive layer can be embodied in a plurality of regions of the breast fixation element, in particular for fastening to the support surface.

According to one or more example embodiments of the present invention, the fastening element includes Velcro fastening, elastic tape, a snap fastener, a click fastener, a loop or a double loop. In the embodiments including Velcro fastening, elastic tape, a snap fastener, a click fastener, a loop or a double loop, a further fastening element can be provided on the support surface with which the fastening element can engage and, in this way, establish a connection between the breast fixation element and the support surface. In the case of Velcro fastening, it is in particular possible for the rough surface to be attached to the support surface while the soft surface is attached to the breast fixation element. Advantageously, this can avoid scratching of the skin. In the case of elastic tape, the elastic tape can be stretched around the housing of the X-ray detector or between buttons, rails or other fastening means for the elastic tape. In the case of a snap fastener or click fastener, a corresponding counterpart can be provided on the support surface. In the case of a loop or double loop, hooks or buttons can be provided on the support surface. Advantageously, a detachable connection can be established between the breast fixation element and the support surface.

According to one or more example embodiments of the present invention, the fastening element can be fastened to the support surface on the upper side, a side surface or to the underside of the support surface. The support surface can in particular be embodied as a housing of the X-ray detector, preferably the surface facing the X-ray source. The fastening element can in particular be fastened on the upper side, a side surface or the underside of the housing of the X-ray detector or brought into connection with the support surface.

According to one or more example embodiments of the present invention, the surface element is moistened. Advantageously, adhesion can be reinforced.

According to one or more example embodiments of the present invention, the surface element, preferably the breast fixation element, is semi-transparent or partially transparent. Advantageously, it is possible to check whether a skin fold has formed under the breast fixation element during fixation.

According to one or more example embodiments of the present invention, the surface element has at least one perforation for adaptation to the contour of the breast. The perforation can be used to influence stretchability. The perforation can be used to tear the breast fixation element for adaptation to the individual breast.

According to one or more example embodiments of the present invention, the shape of the surface element is adapted to the imaging position. The shape of the surface element and in particular the shape of the breast fixation element can be adapted to the imaging position. In particular, different shapes of the breast fixation element can be provided for craniocaudal and mediolateral (oblique) imaging positions. In addition, the shape and also the size can be adapted to the size of the breast. For example, different sizes can be provided. This can improve both comfort and image quality.

One or more example embodiments of the present invention further relates to a mammography system having a breast fixation element according to one or more example embodiments of the present invention. The support surface can in particular be embodied such that the fastening element can be fastened thereto. Advantageously, the advantages of the breast fixation element can be transferred to the mammography system.

FIG. 1 shows an exemplary embodiment of the breast fixation element 1 according to the invention in a first embodiment. The breast fixation element 1 for a mammography system has a flat elastic surface element with a fastening element for fixing the breast to a support surface 2 of the mammography system, wherein the flat shape of the breast fixation element 1 is adapted to the shape of a breast.

To achieve the best fixation results, it can be particularly advantageous to manufacture or provide the surface element in the shape of a breast or adapted to the shape of the breast. The carrier material or the surface element can be perforated with perforations parallel to the chest wall in order to ensure successive fastening from the side of the chest wall in the direction of the nipple and beyond. Herein, the perforation 5 can be embodied in a line parallel to the edge of the breast fixation element 1, which, in use, extends parallel to the chest wall. The perforation 5 can in particular be embodied at a distance from the edge of the breast fixation element 1, wherein the distance can be selected such that at least more than half of the breast volume can be arranged between the edge and the distance. Thus, in the sloping region of the breast 4 toward the nipple, the shape of the breast fixation element 1 can be adapted to the individual shape of the breast in a simplified manner via the perforation 5. The carrier material or the surface element can be perforated along the dashed lines in order to ensure successive fastening from the side of the chest wall in the direction of the nipple and beyond.

Furthermore, different sizes and shapes of the breast fixation elements 1 can be provided to enable a breast fixation element 1 according to one or more example embodiments of the present invention to be used in a particularly advantageous manner for different breast sizes and different positions, such as craniocaudal and mediolateral (oblique) positions. A further perforation 5 can be embodied in the region of the nipple parallel to the edge.

Viewed from the edge, the shape of the breast fixation element 1 can include an initially rectangular region 6, the longer edge of which extends along the edge. The rectangular region 6 can be adjoined by a rounded region 7, which, for example, can be embodied as approximately semicircular in shape. Herein, the edge of the semicircle can adjoin the rectangular region 6. This can be adjoined by a narrower second rectangular region 8 in extension to the center of the semicircle, wherein the short edge of the second rectangular region 8 adjoins the semicircle, wherein a perforation 5 can be embodied at the transition between the semicircular region 7 and the second rectangular region 8. Viewed from the first rectangular region 6, the semicircular region 7 can be embodied as centered, in particular for an embodiment for craniocaudal imaging. The two rectangular regions can at least partially be used for fastening to the support surface 2, in particular the regions that overlap the breast.

FIG. 2 shows an exemplary embodiment of the breast fixation element 1 according to the invention in a second embodiment. Viewed from the first rectangular region 6, the semicircular region 7 can be embodied as non-centered, in particular for an embodiment for mediolateral (oblique) imaging.

Figure 3:
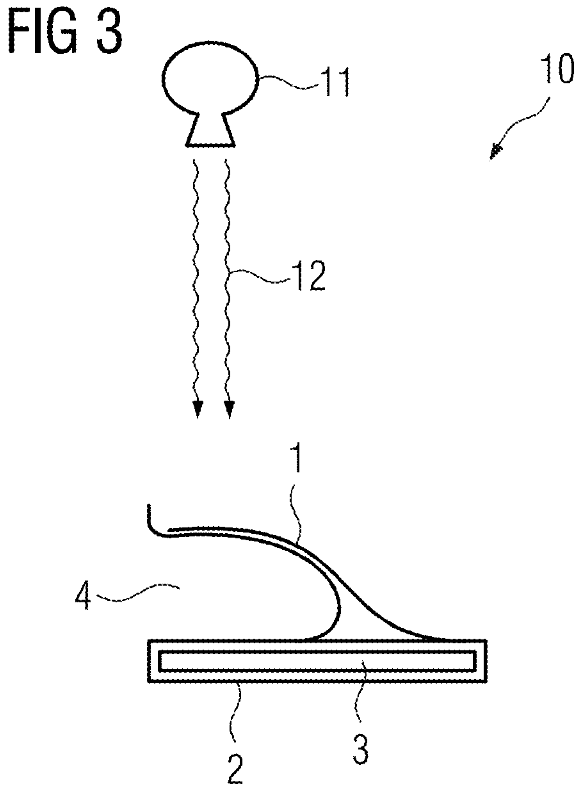
FIG. 3 a schematic representation of the mammography system according to one or more example embodiments of the invention.

FIG. 3 shows an exemplary embodiment of the mammography system 10 according to the invention. The mammography system 10 has an X-ray source 11 which emits X-rays 12. In addition, the mammography system 10 has an X-ray detector 3 which is accommodated in a housing with a support surface 2. The breast 4 is positioned on the support surface 2 and fixed via the breast fixation element 1.

Figure 4:
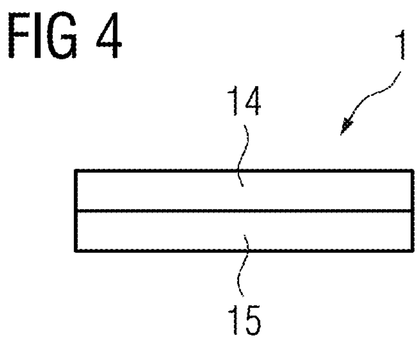
FIG. 4 a schematic representation of the breast fixation element according to the invention in a third embodiment.

FIG. 4 shows an exemplary embodiment of the breast fixation element 1 according to the invention in a third embodiment. In a preferred embodiment, the breast fixation element 1 has a surface element 14 and a fastening element 15 connected thereto over the entire surface. Preferably, the breast fixation element 1 has kinesiology tape as material, which comprises the surface element 14 and the fastening element 15.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc.

Specific structural and functional details disclosed herein are merely representative for purposes of describing example embodiments. The present invention may, however, be embodied in many alternate forms and should not be construed as limited to only the embodiments set forth herein.

Although the invention was illustrated in more detail by the preferred exemplary embodiment, the invention is not restricted by the disclosed examples and other variations can be derived herefrom by the person skilled in the art without departing from the scope of protection of the invention.

The invention claimed is:

1. A breast fixation element for a mammography system comprising:

a flat elastic surface element including a fastening element for fixing a breast to a support surface of the mammography system, wherein a shape of the breast fixation element is adapted to a shape of the breast, the fastening element is an adhesive layer on an underside of the flat elastic surface element, and the flat elastic surface element is removably couplable to the support surface and the breast via the adhesive layer.

2. The breast fixation element of claim 1, wherein the breast fixation element comprises kinesiology tape.

3. The breast fixation element of claim 1, wherein the breast fixation element comprises nylon, Lycra, elastic or cotton.

4. The breast fixation element of claim 1, wherein a shape of the flat elastic surface element is adapted to the breast.

5. The breast fixation element of claim 1, wherein a shape of the flat elastic surface element is square, rectangular, round or triangular.

6. The breast fixation element of claim 1, wherein the fastening element comprises Velcro fastening, elastic tape, a snap fastener, a click fastener, a loop or a double loop.

7. The breast fixation element of claim 1, wherein the fastening element is fastenable to the support surface on an upper side of the support surface, a side surface of the support surface, or on an underside of the support surface.

8. The breast fixation element of claim 1, wherein the flat elastic surface element is moistened.

9. The breast fixation element of claim 1, wherein the flat elastic surface element is semi-transparent or partially transparent.

10. The breast fixation element of claim 1, wherein the flat elastic surface element comprises at least one perforation for adaptation to a contour of the breast.

11. The breast fixation element of claim 1, wherein a shape of the flat elastic surface element is adapted to an imaging position.

12. A mammography system having the breast fixation element of claim 1.

13. The breast fixation element of claim 3, wherein a shape of the flat elastic surface element is adapted to the breast.

14. The breast fixation element of claim 13, wherein a shape of the flat elastic surface element is square, rectangular, round or triangular.

15. A breast fixation element for a mammography system comprising:

a flat elastic surface element including a fastening element for fixing a breast to a support surface of the mammography system, wherein a shape of the breast fixation element is adapted to a shape of the breast and the flat elastic surface element is moistened.

* * * * *